United States Patent
Babkes et al.

(10) Patent No.: US 9,539,133 B2
(45) Date of Patent: Jan. 10, 2017

(54) STOMACH-SPANNING GASTRIC IMPLANTS

(71) Applicant: Apollo Endosurgery, Inc., Austin, TX (US)

(72) Inventors: Mitchell H. Babkes, Santa Clarita, CA (US); Zachary Dominguez, Santa Barbara, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 349 days.

(21) Appl. No.: 13/931,561

(22) Filed: Jun. 28, 2013

(65) Prior Publication Data

US 2013/0289466 A1 Oct. 31, 2013

Related U.S. Application Data

(63) Continuation of application No. 13/275,170, filed on Oct. 17, 2011, now abandoned.
(Continued)

(51) Int. Cl.
*A61F 2/04* (2013.01)
*A61F 5/00* (2006.01)

(52) U.S. Cl.
CPC ............ *A61F 5/0036* (2013.01); *A61F 5/003* (2013.01); *A61F 5/0033* (2013.01);
(Continued)

(58) Field of Classification Search
CPC ................................ A61F 5/0076; A61F 2/04
See application file for complete search history.

(56) References Cited

U.S. PATENT DOCUMENTS

| 1,702,974 A | 2/1929 | MacDonald |
| 2,087,604 A | 7/1937 | Mosher |

(Continued)

FOREIGN PATENT DOCUMENTS

| CN | 1250382 A | 4/2000 |
| CN | 1367670 A | 9/2002 |

(Continued)

OTHER PUBLICATIONS

Xanthakos et al.; "Bariatric Surgery for Extreme Adolescent Obesity: Indications, Outcomes, and Physiologic Effects on the Gut-Brain Axis"; Pathophysiology; V. 15; pp. 135-146; 2008.
(Continued)

*Primary Examiner* — Philip R Wiest
*Assistant Examiner* — Sara Sass
(74) *Attorney, Agent, or Firm* — Gordon & Jacobson, P.C.

(57) ABSTRACT

A variety of passive intragastric implant devices for obesity treatment are disclosed. Such passive implants do not autonomously change shape, but instead react within the stomach to induce satiety. The implants may take up volume within the stomach, thus reducing the digestive capacity. Additionally, the implants may contact areas within the stomach, such as the cardia surrounding the esophageal sphincter, to stimulate satiety-inducing nerves. Also, a number of implants slow gastric emptying by blocking or otherwise impeding flow through the pyloric sphincter. Other implants delay digestion by providing a duodenal sleeve. A number of implants combine two or more of these satiety-inducing features. Methods of implant are disclosed including compressing the implants within a delivery tube and transorally advancing the implants through the esophagus to be deployed within the stomach. Removal of the implants occurs in the reverse.

6 Claims, 3 Drawing Sheets

Related U.S. Application Data

(60) Provisional application No. 61/485,009, filed on May 11, 2011, provisional application No. 61/394,592, filed on Oct. 19, 2010.

(52) U.S. Cl.
CPC .......... *A61F 5/0076* (2013.01); *A61F 5/0086* (2013.01); *A61F 5/0079* (2013.01); *A61F 5/0089* (2013.01); *Y10T 24/4453* (2015.01); *Y10T 24/44342* (2015.01); *Y10T 24/44564* (2015.01)

(56) References Cited

U.S. PATENT DOCUMENTS

| | | |
|---|---|---|
| 2,163,048 A | 6/1939 | McKee |
| 2,619,138 A | 11/1952 | Marler |
| 3,667,081 A | 6/1972 | Burger |
| 3,719,973 A | 3/1973 | Bell |
| 3,840,018 A | 10/1974 | Heifetz |
| 3,919,724 A | 11/1975 | Sanders |
| 4,118,805 A | 10/1978 | Reimels |
| 4,364,379 A | 12/1982 | Finney |
| 4,416,267 A | 11/1983 | Garren |
| 4,430,392 A | 2/1984 | Kelley |
| 4,485,805 A | 12/1984 | Foster |
| 4,545,367 A | 10/1985 | Tucci |
| 4,586,501 A | 5/1986 | Claracq |
| 4,592,355 A | 6/1986 | Antebi |
| 4,598,699 A | 7/1986 | Garren |
| 4,607,618 A | 8/1986 | Angelchik |
| 4,636,213 A | 1/1987 | Pakiam |
| 4,648,383 A | 3/1987 | Angelchik |
| 4,694,827 A | 9/1987 | Weiner |
| 4,723,547 A | 2/1988 | Kullas |
| 4,739,758 A | 4/1988 | Lai |
| 4,773,432 A | 9/1988 | Rydell |
| 4,774,956 A | 10/1988 | Kruse |
| 4,844,068 A | 7/1989 | Arata |
| 4,881,939 A | 11/1989 | Newman |
| 4,899,747 A | 2/1990 | Garren |
| 4,925,446 A | 5/1990 | Garay |
| 4,930,535 A | 6/1990 | Rinehold |
| 4,950,258 A | 8/1990 | Kawai |
| 4,969,899 A | 11/1990 | Cox |
| 5,074,868 A | 12/1991 | Kuzmak |
| 5,084,061 A | 1/1992 | Gau |
| 5,211,371 A | 5/1993 | Coffee |
| 5,226,429 A | 7/1993 | Kuzmak |
| 5,255,690 A | 10/1993 | Keith |
| 5,259,399 A | 11/1993 | Brown |
| 5,289,817 A | 3/1994 | Williams |
| 5,308,324 A | 5/1994 | Hammerslag |
| 5,312,343 A | 5/1994 | Krog |
| 5,449,368 A | 9/1995 | Kuzmak |
| 5,514,176 A | 5/1996 | Bosley |
| 5,527,340 A | 6/1996 | Vogel |
| 5,540,701 A | 7/1996 | Sharkey |
| 5,547,458 A | 8/1996 | Ortiz |
| 5,601,604 A | 2/1997 | Vincent |
| 5,658,298 A | 8/1997 | Vincent |
| 5,693,014 A | 12/1997 | Abele |
| 5,725,507 A | 3/1998 | Petrick |
| 5,748,200 A | 5/1998 | Funahashi |
| 5,776,160 A | 7/1998 | Pasricha |
| 5,819,749 A | 10/1998 | Lee |
| 5,820,584 A | 10/1998 | Crabb |
| RE36,176 E | 3/1999 | Kuzmak |
| 5,938,669 A | 8/1999 | Klaiber |
| 6,074,341 A | 6/2000 | Anderson |
| 6,102,678 A | 8/2000 | Peclat |
| 6,102,897 A | 8/2000 | Lang |
| 6,102,922 A | 8/2000 | Jakobsson |
| 6,152,922 A | 11/2000 | Ouchi |
| 6,183,492 B1 | 2/2001 | Hart |
| 6,264,700 B1 | 7/2001 | Kilcoyne |
| 6,290,575 B1 | 9/2001 | Shipp |
| 6,322,538 B1 | 11/2001 | Elbert |
| 6,450,946 B1 | 9/2002 | Forsell |
| 6,454,699 B1 | 9/2002 | Forsell |
| 6,454,785 B2 | 9/2002 | De |
| 6,464,628 B1 | 10/2002 | Forsell |
| 6,470,892 B1 | 10/2002 | Forsell |
| 6,503,264 B1 | 1/2003 | Birk |
| 6,511,490 B2 | 1/2003 | Robert |
| 6,540,789 B1 | 4/2003 | Silverman |
| 6,547,801 B1 | 4/2003 | Dargent |
| 6,579,301 B1 | 6/2003 | Bales |
| 6,629,776 B2 | 10/2003 | Bell |
| 6,675,809 B2 | 1/2004 | Stack |
| 6,682,473 B1 | 1/2004 | Matsuura |
| 6,733,512 B2 | 5/2004 | McGhan |
| 6,733,513 B2 | 5/2004 | Boyle |
| 6,746,460 B2 | 6/2004 | Gannoe |
| 6,776,783 B1 | 8/2004 | Frantzen |
| 6,840,257 B2 | 1/2005 | Dario |
| 6,845,776 B2 | 1/2005 | Stack |
| 6,905,471 B2 | 6/2005 | Leivseth |
| 6,960,233 B1 | 11/2005 | Berg |
| 6,981,978 B2 | 1/2006 | Gannoe |
| 6,981,980 B2 | 1/2006 | Sampson |
| 6,994,095 B2 | 2/2006 | Burnett |
| 7,008,419 B2 | 3/2006 | Shadduck |
| 7,020,531 B1 | 3/2006 | Colliou |
| 7,033,384 B2 | 4/2006 | Gannoe |
| 7,037,344 B2 | 5/2006 | Kagan |
| 7,056,305 B2 | 6/2006 | Garza |
| 7,090,699 B2 | 8/2006 | Geitz |
| 7,214,233 B2 | 5/2007 | Gannoe |
| 7,220,237 B2 | 5/2007 | Gannoe |
| 7,220,284 B2 | 5/2007 | Kagan |
| 7,223,277 B2 | 5/2007 | DeLegge |
| 7,320,696 B2 | 1/2008 | Gazi |
| 7,347,875 B2 | 3/2008 | Levine |
| 7,354,454 B2 | 4/2008 | Stack |
| 7,476,256 B2 | 1/2009 | Meade |
| 7,510,559 B2 | 3/2009 | Deem |
| 7,608,114 B2 | 10/2009 | Levine |
| 7,628,442 B1 | 12/2009 | Spencer |
| 7,682,330 B2 | 3/2010 | Meade |
| 7,695,446 B2 | 4/2010 | Levine |
| 7,699,863 B2 | 4/2010 | Marco |
| 7,753,870 B2 | 7/2010 | Demarais |
| 7,771,382 B2 | 8/2010 | Levine |
| 7,794,447 B2 | 9/2010 | Dann |
| 7,815,589 B2 | 10/2010 | Meade |
| 7,837,643 B2 | 11/2010 | Levine |
| 7,841,503 B2 | 11/2010 | Sonnenschein |
| 7,883,525 B2 | 2/2011 | DeLegge |
| 7,931,693 B2 | 4/2011 | Binmoeller |
| 7,981,162 B2 | 7/2011 | Stack |
| 8,029,455 B2 | 10/2011 | Stack |
| 8,032,223 B2 | 10/2011 | Imran |
| 8,075,582 B2 | 12/2011 | Lointier |
| 8,162,969 B2 | 4/2012 | Brister |
| 8,187,297 B2 | 5/2012 | Makower |
| 8,216,266 B2 | 7/2012 | Hively |
| 2002/0019577 A1 | 2/2002 | Arabia |
| 2002/0055757 A1 | 5/2002 | Torre |
| 2002/0095181 A1 | 7/2002 | Beyar |
| 2002/0139208 A1 | 10/2002 | Yatskov |
| 2002/0183782 A1 | 12/2002 | Tsugita |
| 2003/0045896 A1 | 3/2003 | Murphy |
| 2003/0073880 A1 | 4/2003 | Polsky |
| 2003/0074054 A1 | 4/2003 | Duerig |
| 2003/0100822 A1 | 5/2003 | Lew |
| 2003/0106761 A1 | 6/2003 | Taylor |
| 2003/0109935 A1 | 6/2003 | Geitz |
| 2003/0144575 A1 | 7/2003 | Forsell |
| 2003/0153905 A1 | 8/2003 | Edwards |
| 2003/0158570 A1 | 8/2003 | Ferrazzi |
| 2004/0044357 A1 | 3/2004 | Gannoe |
| 2004/0092892 A1 | 5/2004 | Kagan |
| 2004/0117031 A1 | 6/2004 | Stack |

(56) References Cited

U.S. PATENT DOCUMENTS

| | | | |
|---|---|---|---|
| 2004/0122452 A1 | 6/2004 | Deem | |
| 2004/0122453 A1 | 6/2004 | Deem | |
| 2004/0143342 A1 | 7/2004 | Stack | |
| 2004/0148034 A1 | 7/2004 | Kagan | |
| 2004/0172142 A1* | 9/2004 | Stack | A61F 2/04 623/23.65 |
| 2004/0186503 A1 | 9/2004 | DeLegge | |
| 2005/0033332 A1 | 2/2005 | Burnett | |
| 2005/0049718 A1 | 3/2005 | Dann | |
| 2005/0055039 A1 | 3/2005 | Burnett | |
| 2005/0085923 A1 | 4/2005 | Levine | |
| 2005/0096692 A1 | 5/2005 | Linder | |
| 2005/0110280 A1 | 5/2005 | Guy | |
| 2005/0131485 A1 | 6/2005 | Knudson | |
| 2005/0190070 A1 | 9/2005 | Rudduck | |
| 2005/0192614 A1 | 9/2005 | Binmoeller | |
| 2005/0192615 A1 | 9/2005 | Torre | |
| 2005/0197714 A1 | 9/2005 | Sayet | |
| 2005/0228504 A1 | 10/2005 | Demarais | |
| 2005/0240279 A1 | 10/2005 | Kagan | |
| 2005/0250979 A1 | 11/2005 | Coe | |
| 2005/0256533 A1 | 11/2005 | Roth | |
| 2005/0261711 A1 | 11/2005 | Okada | |
| 2005/0267595 A1 | 12/2005 | Chen | |
| 2005/0267596 A1 | 12/2005 | Chen | |
| 2005/0273060 A1 | 12/2005 | Levy | |
| 2005/0277975 A1 | 12/2005 | Saadat | |
| 2006/0020278 A1 | 1/2006 | Burnett | |
| 2006/0025799 A1 | 2/2006 | Basu | |
| 2006/0069403 A1 | 3/2006 | Shalon | |
| 2006/0106288 A1 | 5/2006 | Roth | |
| 2006/0142700 A1 | 6/2006 | Sobelman | |
| 2006/0178691 A1 | 8/2006 | Binmoeller | |
| 2006/0190019 A1 | 8/2006 | Gannoe | |
| 2006/0217762 A1 | 9/2006 | Maahs | |
| 2006/0229702 A1 | 10/2006 | Agnew | |
| 2006/0252983 A1 | 11/2006 | Lembo | |
| 2007/0010864 A1 | 1/2007 | Dann | |
| 2007/0016262 A1 | 1/2007 | Gross | |
| 2007/0021761 A1 | 1/2007 | Phillips | |
| 2007/0078476 A1 | 4/2007 | Hull | |
| 2007/0083224 A1 | 4/2007 | Hively | |
| 2007/0100368 A1 | 5/2007 | Quijano | |
| 2007/0118168 A1 | 5/2007 | Lointier | |
| 2007/0135803 A1 | 6/2007 | Belson | |
| 2007/0135829 A1 | 6/2007 | Paganon | |
| 2007/0147170 A1 | 6/2007 | Hood | |
| 2007/0149994 A1 | 6/2007 | Sosnowski | |
| 2007/0156013 A1 | 7/2007 | Birk | |
| 2007/0156248 A1 | 7/2007 | Marco | |
| 2007/0173881 A1 | 7/2007 | Birk | |
| 2007/0185374 A1 | 8/2007 | Kick | |
| 2007/0185375 A1 | 8/2007 | Stad | |
| 2007/0239284 A1 | 10/2007 | Skerven | |
| 2007/0250020 A1 | 10/2007 | Kim | |
| 2007/0265598 A1 | 11/2007 | Karasik | |
| 2007/0276428 A1 | 11/2007 | Haller | |
| 2007/0288033 A1 | 12/2007 | Murature | |
| 2007/0293716 A1 | 12/2007 | Baker | |
| 2008/0015618 A1 | 1/2008 | Sonnenschein | |
| 2008/0058840 A1 | 3/2008 | Albrecht | |
| 2008/0058887 A1 | 3/2008 | Griffin | |
| 2008/0065122 A1 | 3/2008 | Stack | |
| 2008/0071305 A1 | 3/2008 | DeLegge | |
| 2008/0097513 A1 | 4/2008 | Kaji | |
| 2008/0167606 A1 | 7/2008 | Dann | |
| 2008/0172079 A1 | 7/2008 | Birk | |
| 2008/0208240 A1 | 8/2008 | Paz | |
| 2008/0208241 A1 | 8/2008 | Weiner | |
| 2008/0221595 A1 | 9/2008 | Surti | |
| 2008/0228205 A1 | 9/2008 | Sharkey | |
| 2008/0234718 A1 | 9/2008 | Paganon | |
| 2008/0234834 A1 | 9/2008 | Meade | |
| 2008/0243071 A1 | 10/2008 | Quijano | |
| 2008/0243166 A1 | 10/2008 | Paganon | |
| 2008/0249635 A1 | 10/2008 | Weitzner | |
| 2008/0255601 A1 | 10/2008 | Birk | |
| 2008/0255678 A1 | 10/2008 | Cully | |
| 2008/0262529 A1 | 10/2008 | Jacques | |
| 2008/0306506 A1 | 12/2008 | Leatherman | |
| 2009/0012553 A1* | 1/2009 | Swain et al. | 606/191 |
| 2009/0082644 A1 | 3/2009 | Li | |
| 2009/0093767 A1 | 4/2009 | Kelleher | |
| 2009/0093837 A1 | 4/2009 | Dillon | |
| 2009/0131968 A1 | 5/2009 | Birk | |
| 2009/0132031 A1 | 5/2009 | Cook | |
| 2009/0149879 A1 | 6/2009 | Dillon | |
| 2009/0177215 A1 | 7/2009 | Stack | |
| 2009/0198210 A1 | 8/2009 | Burnett | |
| 2009/0216337 A1* | 8/2009 | Egan et al. | 623/23.64 |
| 2009/0259246 A1 | 10/2009 | Eskaros | |
| 2009/0275973 A1 | 11/2009 | Chen | |
| 2009/0287231 A1 | 11/2009 | Brooks | |
| 2009/0299327 A1 | 12/2009 | Tilson | |
| 2009/0299486 A1 | 12/2009 | Shohat | |
| 2009/0312597 A1 | 12/2009 | Bar | |
| 2010/0030017 A1 | 2/2010 | Baker | |
| 2010/0049224 A1 | 2/2010 | Vargas | |
| 2010/0081991 A1 | 4/2010 | Swisher | |
| 2010/0082047 A1 | 4/2010 | Cosgrove | |
| 2010/0087843 A1 | 4/2010 | Bertolote | |
| 2010/0100079 A1 | 4/2010 | Berkcan | |
| 2010/0100115 A1 | 4/2010 | Soetermans | |
| 2010/0121371 A1 | 5/2010 | Brooks | |
| 2010/0168782 A1 | 7/2010 | Hancock | |
| 2010/0168783 A1 | 7/2010 | Murature | |
| 2010/0174307 A1 | 7/2010 | Birk | |
| 2010/0198249 A1 | 8/2010 | Sabliere | |
| 2010/0234937 A1 | 9/2010 | Wang | |
| 2010/0249822 A1 | 9/2010 | Nihalani | |
| 2010/0249825 A1 | 9/2010 | Nihalani | |
| 2010/0256775 A1 | 10/2010 | Belhe | |
| 2010/0256776 A1 | 10/2010 | Levine | |
| 2010/0261390 A1 | 10/2010 | Gardner | |
| 2010/0274194 A1 | 10/2010 | Sobelman | |
| 2010/0286628 A1 | 11/2010 | Gross | |
| 2010/0305590 A1 | 12/2010 | Holmes | |
| 2010/0331756 A1 | 12/2010 | Meade | |
| 2010/0332000 A1 | 12/2010 | Forsell | |
| 2011/0009897 A1 | 1/2011 | Forsell | |
| 2011/0106113 A1 | 5/2011 | Tavakkolizadeh | |
| 2011/0307075 A1 | 12/2011 | Sharma | |
| 2012/0022561 A1 | 1/2012 | Forsell | |
| 2012/0095483 A1 | 4/2012 | Babkes | |
| 2012/0221037 A1 | 8/2012 | Birk | |

FOREIGN PATENT DOCUMENTS

| | | |
|---|---|---|
| DE | 8804765 U1 | 5/1989 |
| DE | 102007025312 A1 | 11/2008 |
| EP | 1396242 A1 | 3/2004 |
| EP | 1396243 A1 | 3/2004 |
| EP | 1397998 A1 | 3/2004 |
| EP | 1774929 A2 | 4/2007 |
| EP | 2095798 | 9/2009 |
| FR | 2797181 A1 | 2/2001 |
| FR | 2823663 A1 | 10/2002 |
| FR | 2852821 A1 | 10/2004 |
| FR | 2855744 A1 | 12/2004 |
| FR | 2892297 A1 | 4/2007 |
| FR | 2941617 A1 | 8/2010 |
| GB | 2086792 A | 5/1982 |
| JP | S63279854 A | 11/1988 |
| JP | 1049572 A | 2/1989 |
| JP | 63264078 | 10/1998 |
| WO | 8800027 | 1/1988 |
| WO | 8800027 A1 | 1/1988 |
| WO | 0015158 A1 | 3/2000 |
| WO | 0032092 | 6/2000 |
| WO | 0110359 A1 | 2/2001 |
| WO | 0149245 A2 | 7/2001 |
| WO | 0166166 A2 | 9/2001 |
| WO | 0235980 A2 | 5/2002 |
| WO | 03055419 A1 | 7/2003 |

(56) References Cited

FOREIGN PATENT DOCUMENTS

| | | |
|---|---|---|
| WO | 03105732 A1 | 12/2003 |
| WO | 2004019671 A2 | 3/2004 |
| WO | 2005007231 A1 | 1/2005 |
| WO | 2005094257 A2 | 10/2005 |
| WO | 2005097012 | 10/2005 |
| WO | 2005097012 A2 | 10/2005 |
| WO | 2005110280 | 11/2005 |
| WO | 2005110280 A2 | 11/2005 |
| WO | 2006044640 A1 | 4/2006 |
| WO | 2006020370 | 6/2006 |
| WO | 2006063593 A2 | 6/2006 |
| WO | 2006090018 A1 | 8/2006 |
| WO | 2006111961 A2 | 10/2006 |
| WO | 2006118744 A1 | 11/2006 |
| WO | 2007027812 A2 | 3/2007 |
| WO | 2007053556 A1 | 5/2007 |
| WO | 2007076021 A2 | 7/2007 |
| WO | 2007092390 A2 | 8/2007 |
| WO | 2007110866 A2 | 10/2007 |
| WO | 2008101048 A2 | 8/2008 |
| WO | 2008112894 A1 | 9/2008 |
| WO | 2008132745 A2 | 11/2008 |
| WO | 2010042062 A1 | 4/2010 |
| WO | 2010074712 | 7/2010 |
| WO | 2010074712 A2 | 7/2010 |
| WO | 2010087757 A1 | 8/2010 |
| WO | 2010117641 A2 | 10/2010 |

OTHER PUBLICATIONS

Baggio et al. 'Biology of Integrins: GLP-1 and GIP'; Gastroenrology; V. 132; pp. 2131-2157; 2007.

Berne et al; 'Physiology'; V. 5; pp. 55-57, 210, 428, 540, 554, 579, 584, 591; 2004.

Boulant et al.; 'Cholecystokinin in Transient Lower Oesophageal Sphincter Relation Due to Gastric Distension in Humans'; Gut; V. 40; pp. 575-581; 1997.

Bradjewin et al; 'Dose Ranging Study of the Effects of Cholecystokinin in Healthy Volunteers'; J. Psychiatr. Neurosci.; V. 16 (2); pp. 91-95; 1991.

Chaudhri; 'Can Gut Hormones Control Appetite and Prevent Obesity?' Diabetes Care; V. 31; Supp 2; pp. S284-S289; Feb. 2008.

Cohen et al.; 'Oxyntomodulin Suppresses Appetite and Reduces Food in Humans'; J. Clin. Endocrinol. Metab.; V. 88; pp. 4696-4701; 2003.

Dakin et al.; 'Oxyntomodulin Inhibits Food Intake in the Rat'; Endocrinology; V. 142; pp. 4244-4250; 2001.

Dakin et al.; 'Peripheral Oxyntomodulin Reduces Food Intake and Body Weight gain in Rats'; Endocrinology; V. 145; No. 6; pp. 2687-2695; Jun. 2004.

Davison; 'Activation of Vagal-Gastric Mechanoreceptors by Cholecystokinin'; Proc. West. Pharmocol. Soc; V. 29; pp. 363-366; 1986.

Ekblad et al.; 'Distribution of Pancreatic Peptide and Peptide-YY'; Peptides; V. 23; pp. 251-261;2002.

Greenough et al.; 'Untangling the Effects of Hunger, Anxiety and Nausea on Energy Intake During Intravenous Cholecystokinin Octapeptide (CCK-8) Infusion' Physiology and Behavior; V. 65 (2); pp. 303-310; 1998.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Houpt; 'Gastrointestinal Factors in Hunger and Satiety'; Neurosci. and Behav. Rev.; V. 6; pp. 145-164; 1982.

Kissileff et al.; 'Peptides that Regulate Food Intake: Cholecystokinin and Stomach Distension Combine to Reduce Food Intake in Humans'; Am. J. Physiol. Regul. lntegr. Comp. Physiol.; V. 285; pp. 992-998; 2003.

Naslund et al.; 'Prandial Subcutaneous Injection of Glucagon-Like Peptide'; Br. J. Nutr.; V. 91; pp. 439-446; 2004.

Renshaw et al. 'Peptide YY: A Potential Therapy for Obesity'; Current Drug Targets; V. 6; pp. 171-179; 2005.

Verdich et al. 'A Meta-Analysis of the Effect of Glucagon-Like-Peptide-1 (7-36) Amide on ad Libitum Energy Intake in Humans'; J. Clin. Endocrinal. Metab. V. 86; pp. 4382-4389; Sep. 2001.

Wynne et al.; 'Subcutaneous Oxyntomodulin Reduces Body Weight in Overweight and Obese Subiects: A Double-Blind Randomized, Controlled Trial'; Diabetes; V. 54; pp. 2390-2395; 2005.

BIB Bioenterics Intragastric Balloon Program, 'Take Control of Your Weight and Your Life/The Solution for You,' (named Health, pp. 1-2; Jan. 19, 2004.

BIB Bioenterics Intragastric Balloon Program, 'Taking the Next Step/Take Control of Your Weight and Your Life,' Inamed Health, pp. 1-9; Apr. 29, 2004.

BIB Data Sheet Directions for Use, 'BioEnterics Intragastric Balloon System,' Inamed Health, 1-12 pp.

'Living With the BIB/BioEnterics Intragastric Balloon Program,' Inamed Health; 1-10 Patient Information Brochure; pp.; May 1, 2005.

* cited by examiner

STOMACH-SPANNING GASTRIC IMPLANTS

RELATED APPLICATIONS

The present application is a continuation of U.S. patent application Ser. No. 13/275,170, filed Oct. 17, 2011, which claims priority under 35 U.S.C. §119 to U.S. Provisional Application No. 61/485,009, filed May 11, 2011, and to 61/394,592, filed Oct. 19, 2010, the disclosures of which are incorporated by reference herein.

FIELD OF THE INVENTION

The present invention is directed to intragastric implants used for the treatment of obesity, and in particular to implants for placement in and spanning the stomach cavity.

BACKGROUND OF THE INVENTION

Over the last 50 years, obesity has been increasing at an alarming rate and is now recognized by leading government health authorities, such as the Centers for Disease Control (CDC) and National Institutes of Health (NIH), as a disease. In the United States alone, obesity affects more than 60 million individuals and is considered the second leading cause of preventable death. Worldwide, approximately 1.6 billion adults are overweight, and it is estimated that obesity affects at least 400 million adults.

Obesity is caused by a wide range of factors including genetics, metabolic disorders, physical and psychological issues, lifestyle, and poor nutrition. Millions of obese and overweight individuals first turn to diet, fitness and medication to lose weight; however, these efforts alone are often not enough to keep weight at a level that is optimal for good health. Surgery is another increasingly viable alternative for those with a Body Mass Index (BMI) of greater than 40. In fact, the number of bariatric surgeries in the United States was estimated to be about 400,000 in 2010.

Examples of surgical methods and devices used to treat obesity include the LAP-BAND® (Allergan Medical of Irvine, Calif.) gastric band and the LAP-BAND AP® (Allergan). However, surgery might not be an option for every obese individual; for certain patients, non-surgical therapies or minimal-surgery options are more effective or appropriate.

In the early 1980s, physicians began to experiment with the placement of intragastric balloons to reduce the size of the stomach reservoir, and consequently its capacity for food. Once deployed in the stomach, the balloon helps to trigger a sensation of fullness and a decreased feeling of hunger. These devices are designed to provide therapy for moderately obese individuals who need to shed pounds in preparation for surgery, or as part of a dietary or behavioral modification program. These balloons are typically cylindrical or pear-shaped, generally range in size from 200-500 ml or more, are made of an elastomer such as silicone, polyurethane, or latex, and are filled with air, an inert gas, water, or saline.

One such inflatable intragastric balloon is described in U.S. Pat. No. 5,084,061 and is commercially available as the BioEnterics Intragastric Balloon System ("BIB System," sold under the trademark ORBERA). The BIB System comprises a silicone elastomer intragastric balloon that is inserted into the stomach and filled with fluid. Conventionally, the balloons are placed in the stomach in an empty or deflated state and thereafter filled (fully or partially) with a suitable fluid. The balloon occupies space in the stomach, thereby leaving less room available for food and creating a feeling of satiety for the patient. Placement of the intragastric balloon is non-surgical, trans-oral, usually requiring no more than 20-30 minutes. The procedure is performed gastroscopically in an outpatient setting, typically using local anesthesia and sedation. Placement of such balloons is temporary, and such balloons are typically removed after about six months. Removing the balloon requires deflation by puncturing with a gastroscopic instrument, and either aspirating the contents of the balloon and removing it, or allowing the fluid to pass into the patient's stomach. Clinical results with these devices show that for many obese patients, the intragastric balloons significantly help to control appetite and accomplish weight loss.

Some attempted solutions for weight loss by placing devices in the stomach result in unintended consequences. For instance, some devices tend to cause food and liquid to back up in the stomach, leading to symptoms of gastroesophageal reflux disease (GERD), a condition in which the stomach contents (food or liquid) leak backwards from the stomach into the esophagus. Also, the stomach acclimates to some gastric implant devices, leading to an expansion of stomach volume and consequent reduction in the efficacy of the device.

Therefore, despite many advances in the design of intragastric obesity treatment implants, there remains a need for improved devices that can be implanted for longer periods than before or otherwise address certain drawbacks of intragastric balloons and other such implants.

SUMMARY OF THE INVENTION

The present invention addresses the above-described problems by providing passive intragastric apparatuses and methods for inducing satiety and therefore treating obesity. Such passive devices do not autonomously change shape, but instead react within the stomach to induce satiety. The devices may reduce volume within the stomach, thus reducing the digestive capacity. Additionally, the devices may contact areas within the stomach, such as the cardia surrounding the esophageal sphincter, to stimulate satiety-inducing nerves. Also, a number of devices slow gastric emptying by blocking or otherwise impeding flow through the pyloric sphincter. Other devices delay digestion by providing a duodenal sleeve. A number of devices combine two or more of these satiety-inducing features. Methods of implant are disclosed including compressing the devices within a delivery tube and transorally advancing the devices through the esophagus to be deployed within the stomach. Removal of the devices occurs in the reverse.

Each of the implants described herein is formed of materials that permit it to be compressed into a substantially linear transoral delivery configuration and that will resist degradation over a period of at least six months within the stomach.

In accordance with a first embodiment, a passive intragastric obesity treatment implant comprises an esophageal stent sized to anchor within the esophagus just above the esophageal sphincter. A tubular body has a length sufficient to extend between the esophageal sphincter and the pyloric sphincter upon implant in the stomach, the tubular body having perforations therein to permit ingress of stomach juices. A duodenal tube extends in series from the tubular body. Collapsible tubular connectors extend between the esophageal stent and the tubular body, and between the tubular body and the duodenal tube, the connectors each having longitudinal slits therein. Finally, a bulbous flange surrounds and connects to the distal end of the tubular body, the bulbous flange having a size that prevents passage through the pyloric sphincter. The implant may further include an enlargement surrounding the duodenal tube and sized to prevent passage through the pyloric sphincter. The duodenal tube and enlargement may extend only up to 5-10 cm in length. The implant desirably further includes perforations along the tubular body to allow ingress of digestive stomach juices. The bulbous flange is preferably molded with relatively thick walls to maintain its as-molded shape without inflation. In one embodiment, the entire implant is made of silicone.

Another passive intragastric obesity treatment implant disclosed herein has an esophageal stent sized to anchor within the esophagus just above the esophageal sphincter. A tubular body has a length sufficient to extend between the esophageal sphincter and the pyloric sphincter upon implant in the stomach, the esophageal stent attaching to a proximal end of the tubular body with a first tether. The tubular body has perforations therein to permit ingress of stomach juices. A duodenal sleeve extends distally from the tubular body and attaches to the distal end of the tubular body with a second tether. Proximal and distal circular shelves surround free ends of the tubular body, the shelves having sizes that resist passage through the esophageal sphincter and the pyloric sphincter, respectively. Finally, a plurality of positioning rings attach to mid-portions of the tubular body, the positioning rings having a sufficient diameter so as to contact the interior stomach walls upon contraction thereof. The esophageal stent desirably comprises a helical coil of plastic wire. The first tether may be an extension of the helical coil of plastic wire. There are preferably positioning rings on both sides of the tubular body to maintain spacing of the tubular body with walls of the stomach and ensure the tubular body tracks a gradual arc from the esophageal sphincter to the pylorus rather than taking the shortest path. Also, the tubular body and positioning rings are preferably molded together from the same material. Indeed, the entire implant may be made of silicone.

Another passive intragastric obesity treatment implant of the present application has a cardia flange sized and shaped to conform to a cardia region of the stomach and resist passage through the esophageal sphincter and having a central through hole centered at the esophageal sphincter through which food passes. An antrum stent sized and shaped to conform closely to the antrum connects to the cardia flange via a plurality of struts that are flexible enough to straighten out and be passed transorally down an access tube, while also being somewhat stiff to provide light pressure to both the cardia flange and antrum stent on each end. The cardia flange is preferably a flexible, flat partial conical ring that includes a central through hole. The cardia flange may be formed by a braided NITINOL wire mesh covered with a soft silicone. The antrum stent may also be formed by a braided NITINOL wire mesh covered with a soft silicone. The implant preferably further comprises a narrow neck region attached to a distal end of the antrum stent that fits within the pylorus. Further, a duodenal stent may be connected in series with the antrum stent at a narrow neck region such that a generally hourglass shape of the antrum stent, neck region, and duodenal stent conforms closely to the antrum, pylorus and upper end of the duodenum. In one embodiment, the entire implant is made of silicone and NITINOL.

A further understanding of the nature and advantages of the invention will become apparent by reference to the remaining portions of the specification and drawings.

BRIEF DESCRIPTION OF THE DRAWINGS

Features and advantages of the present invention will become appreciated as the same become better understood with reference to the specification, claims, and appended drawings wherein:

FIG. 1A is a perspective view of the implant of FIG. 1;

FIG. 1B is an enlarged sectional view through a portion of FIG. 1;

FIG. 1C is an enlarged sectional view through an alternative distal end configuration for the implant shown in FIG. 1;

DETAILED DESCRIPTION OF THE PREFERRED EMBODIMENTS

The present invention is directed to a variety of different intragastric implants that passively treat obesity by taking up space within the stomach or contact areas in and around the stomach to induce feelings of satiety. Furthermore, some implants described herein affect the rate of stomach emptying. It should be understood that a number of the disclosed implants provide more than one of these passive aspects, and also that any disclosed structure could be combined with another disclosed structure unless physically impossible. As such, combinations of the passive satiety-inducing features disclosed herein, even if not explicitly stated, are contemplated. The term "passive" refers primarily to a lack of any moving parts within the implants, but in general to the inert nature of the various devices. A passive implant as defined herein, however, is not one that cannot affect change or stimulate the stomach, but rather one that may do so without any physical or chemical changes to its basic makeup.

Figure 1:
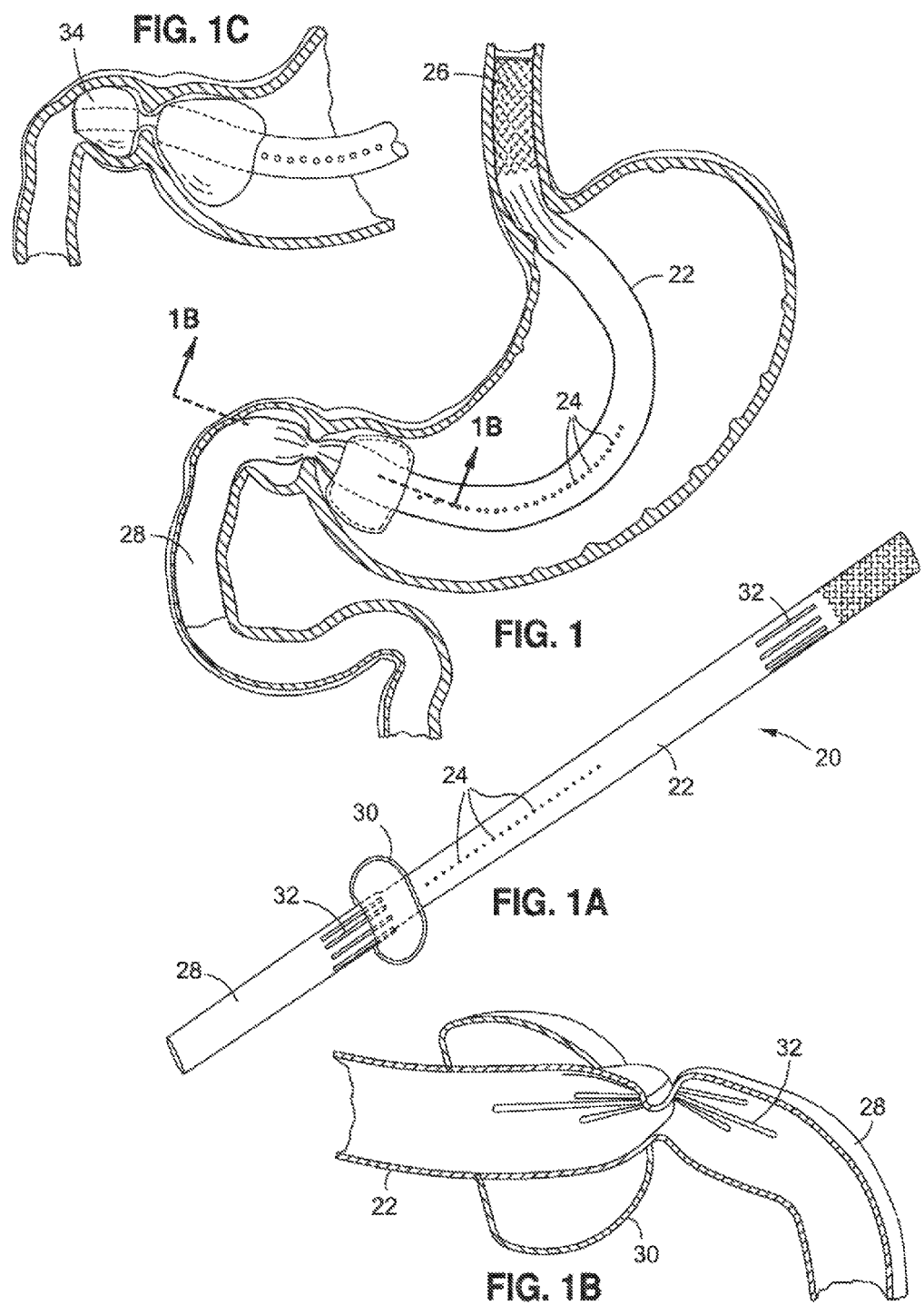
FIG. 1 is a sectional view through a patient's stomach illustrating an implanted stomach-spanning intragastric obesity treatment implant connected to a duodenal sleeve.

FIG. 1 illustrates a first stomach-spanning implant 20, but also illustrates the anatomy of the human stomach, which will be described first. The major function of the stomach is to temporarily store food and release it slowly into the duodenum. The esophagus extending downward from the mouth connects to the stomach via esophageal sphincter, which regulates flow food into the stomach cavity. The cardia surrounds the superior opening of the stomach. The rounded portion superior to the body and adjacent the cardia is the fundus. Inferior to the fundus is the large central portion of the stomach, called the body, that is lined with muscles that contract and relax repetitively to churn the food therein. The stomach processes the food to a semi-solid "chyme," which enables better contact with the mucous membrane of the intestines, thereby facilitating absorption of nutrients. In addition, the stomach is an important site of enzyme production.

Lower down in the stomach the antrum connects the body to the pylorus, which leads into the duodenum. Below the stomach, the duodenum leads into the upper part of the small intestine (not shown); the jejunum makes up about one-third of the small intestine. The region of the stomach that connects to the duodenum is the pylorus. The pylorus communicates with the duodenum of the small intestine via the pyloric sphincter (valve). This valve regulates the passage of chyme from stomach to duodenum and it prevents backflow of chyme from duodenum to stomach.

One general category of passive satiety-inducing implants disclosed herein includes both a space-occupying member and a flow-through channels within the stomach through which solid and liquid flows. One way to look at such artificial intragastric spaces is that they create a stomach-within-stomach.

For example, FIGS. 1-1C disclose a implant 20 configured as a perforated tube 22 that is held in position within the biological stomach, bypassing it and acting as a small, artificial stomach, thereby decreasing the amount of food that is ingestible. Perforations 24 allow ingress of digestive stomach juices. An esophageal stent 26 is built into the tube 22 to anchor the proximal end within the esophagus. A distal sleeve 28 of the tube 22 extends past the pyloric sphincter and empties directly into the duodenum. Pyloric anchoring is achieved by the short duodenal sleeve 28, which also reduces nutrient absorption within the duodenum. To prevent the implant from migrating further down the duodenum, a bulbous flange 30 attaches the tube 22 close to the distal sleeve 28. The bulbous flange 30 is too large to pass through the pyloric sphincter. Desirably, the bulbous flange 30 is molded with relatively thick walls to maintain its as-molded shape without inflation, and may includes holes to allow stomach juices to freely flow in and out.

At the locations where the tube 22 passes through the esophageal and pyloric sphincters, longitudinal slits 32 formed in the walls serve to allow compression of the sphincters and complete closure/sealing. That is, the slits 32 permit the tube 22 to easily buckle inward. Functionality of the slits 32 without damage to the sphincters is dependent on the conformity/pliability and softness of the material from which the tube 22 is manufactured. Desirably, the tube 22 is made of a resilient material that springs outward in the absence of sphincter closing forces, and thus the slits are in substantially constant contact with the surrounding anatomical walls which helps prevent leakage through the slits 32.

Some food will normally "leak" from the esophagus around the bypassing tube 22 into the biological stomach, through the slits, and/or around the esophageal stent 26. The leaked food will likely be small particulate and liquid only, as larger boluses will be naturally steered to and trapped within the tube 22.

Insertion and removal of the implant 20 is accomplished by inserting into the esophagus, a thin-walled, lubricated Teflon tube that is pre-loaded with the compressed implant 20. A distal end of the insertion tube is positioned using visualization techniques within the duodenum, at which point the implant 20 is held from linear movement while the insertion tube is retracted. The esophageal stent 26 anchors and locates the implant 20, and a small amount of repositioning prior to deploying the stent may be required as a final step of implanting the implant 20. To remove, the stent 20 will be grabbed and constricted inward, whereupon the rest of the implant 20 may be withdrawn without too much difficulty.

FIG. 1C is an enlarged sectional view through an alternative distal end configuration for the implant shown in FIG. 1. In this embodiment, the duodenal sleeve 28 is replaced with a much shorter tube enclosed within an enlargement 34, such as an inflated or pillow-like structure. The enlargement 34 prevents migration of the distal to back into the stomach. Although not shown, the short flow-through tube may be extended as far as the sleeve 28 shown in FIG. 1 to reduce the ability of the duodenum to absorb nutrients, thus slowing digestion. In one embodiment, the short duodenal tube and enlargement 34 extend only up to 5-10 cm into the duodenum.

Figure 2:
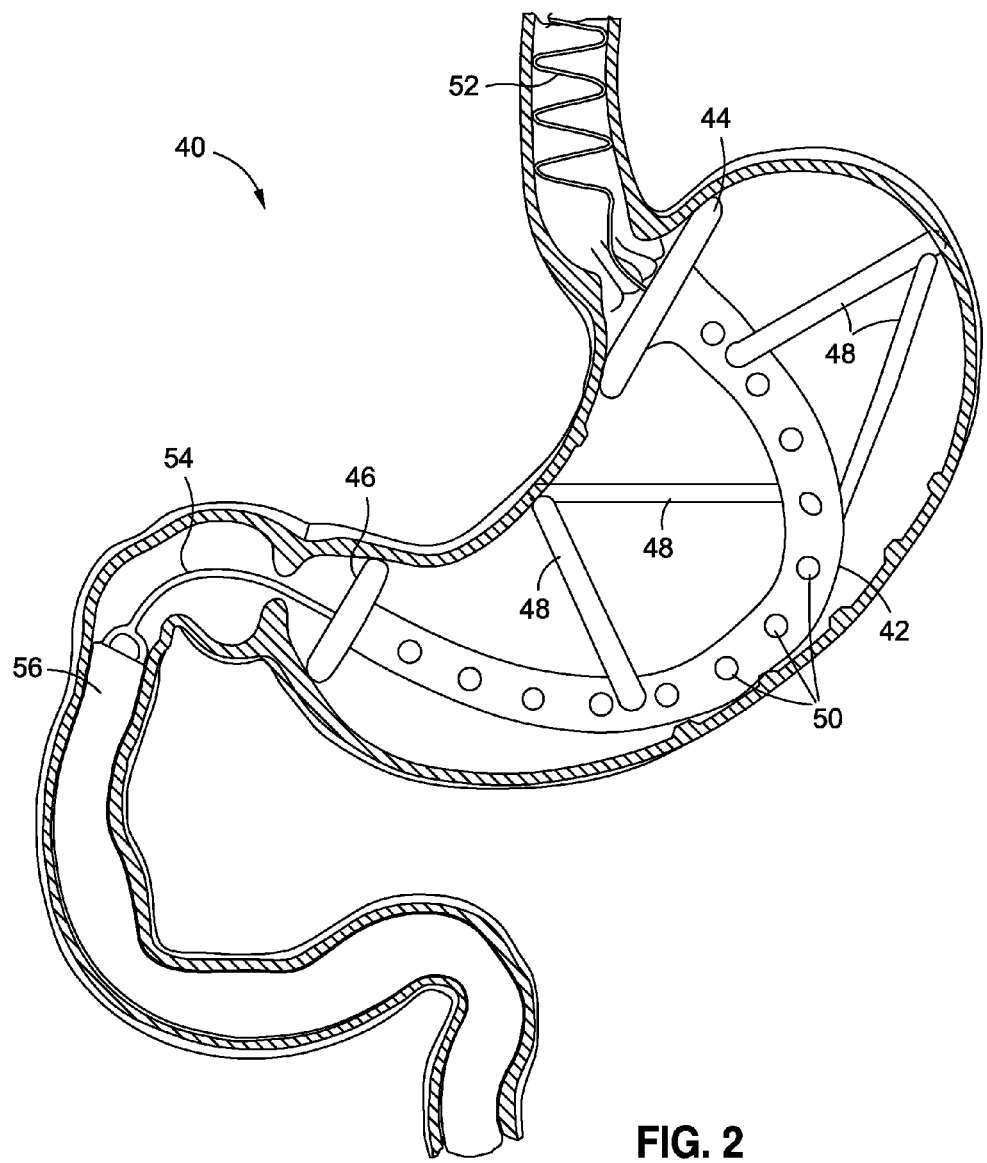
FIG. 2 is a sectional view through a patient's stomach illustrating a further implanted stomach-spanning intragastric obesity treatment implant having positioning rings and shelves, and attached to a duodenal sleeve.

Another so-called stomach-in-stomach implant 40 seen in FIG. 2 provides weight control in three ways—by stimulating the cardia, by providing a stomach-in-stomach, and by providing a duodenal sleeve. The implant 40 comprises an elongated tube 42 having a length that permits it to extend in a curve as show generally from the esophageal sphincter to the pylorus. A proximal shelf 44 surrounding an open proximal end of the tube 42 stabilizes the implant at the esophageal sphincter, while a distal shelf 46 surrounding a distal opening accomplishes the same thing adjacent at the pylorus. These shelves 44, 46 prevent migration back up the esophagus and down the pylorus, respectively. Furthermore, the upper shelf 44 rests firmly against the cardia walls, applying pressure thereto and thereby triggering release of satiety-inducing hormones, signaling the body to stop eating.

The tube 42 is highly flexible and includes a plurality of positioning rings 48 attached thereto, preferably molded into the side wall of the tube. The positioning rings 48 are also highly flexible, so the entire structure can be compressed down into a lubricated introduction tube. The positioning rings provide struts that help maintain the curvature of the tube 42 within the stomach, as shown—in other words, the tube 42 extends in a gradual arc from the esophageal sphincter to the pylorus rather than taking the shortest path. As such, there is preferably at least one positioning ring 48, and more preferably two positioning rings, on the inside curve of the tube 42 to maintain spacing from the lesser curvature of the stomach. Likewise, there is preferably at least one positioning ring 48, and more preferably two positioning rings, on the outside curve of the tube 42 to maintain spacing from the cardia region and greater curvature. Solids and liquids swallowed by the patient enter the tube 42 through the proximal shelf 44 and pass therethrough to exit through the distal shelf 46. Since the tube 42 can hold much less volume than the stomach, smaller than normal amounts of nutrients are able to be processed.

The tube 42 further includes a plurality of fluid transfer perforations 50 that allow digestive juices to freely flow in and out of the tube. Furthermore, peristaltic convolutions of the stomach apply mechanical forces through the tube 42 walls, desirably through the positioning rings 48, to help break down food boluses. Some leakage of food exiting the esophagus into the larger, biological stomach will likely occur, and leakage out through the pylorus will also likely occur. However, most ingested food will likely make its way through this channeling system.

An esophageal stent 52 connected to the proximal shelf 44 helps maintain the preferred position of the implant 40 within the stomach. The stent 52 may be balloon- or self-expanding, and in the illustrated embodiment comprises a helical coil of plastic wire. The esophageal sphincter is allowed to close as normally as possible, since the spiral plastic stent 52 is molded very thinly in the area that passes centrally through the sphincter.

The satiety-inducing implant 40 also restricts caloric intake through the duodenum, as the bottom segment is anchored via an intermediate tether 54 by a duodenal sleeve 56 that lines the upper duodenal wall. Such a duodenal sleeve 56 partially prevents nutrient absorption by inhibiting or delaying the point at which chyme from the stomach contacts the mucous membranes of the intestine.

Figure 3:
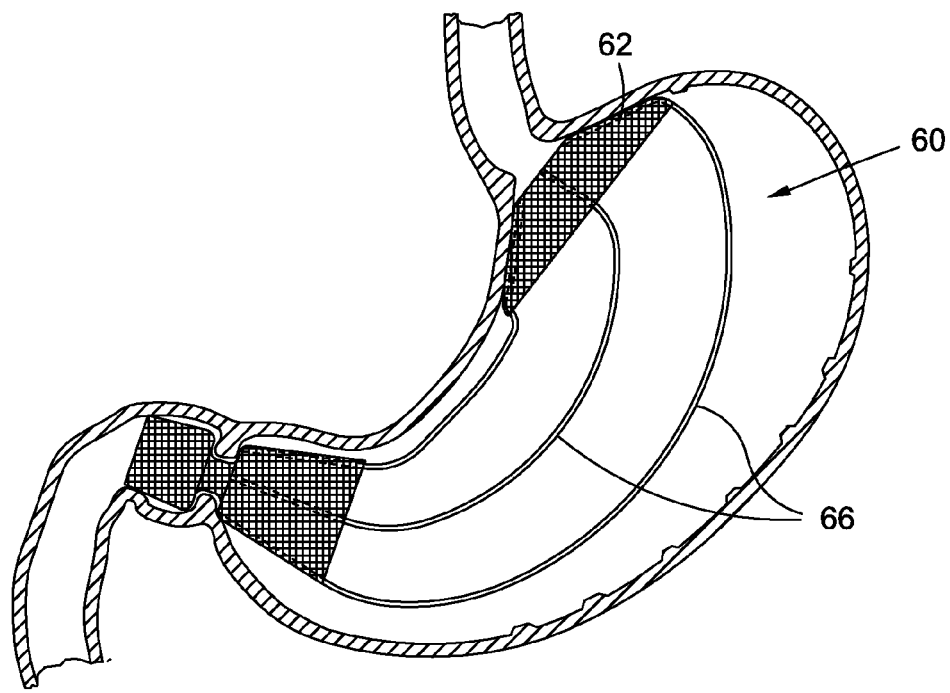
FIG. 3 is a sectional view through a patient's stomach illustrating a still further implanted stomach-spanning intragastric obesity treatment implant having an esophageal flange and a pyloric stent.
Figure 4:
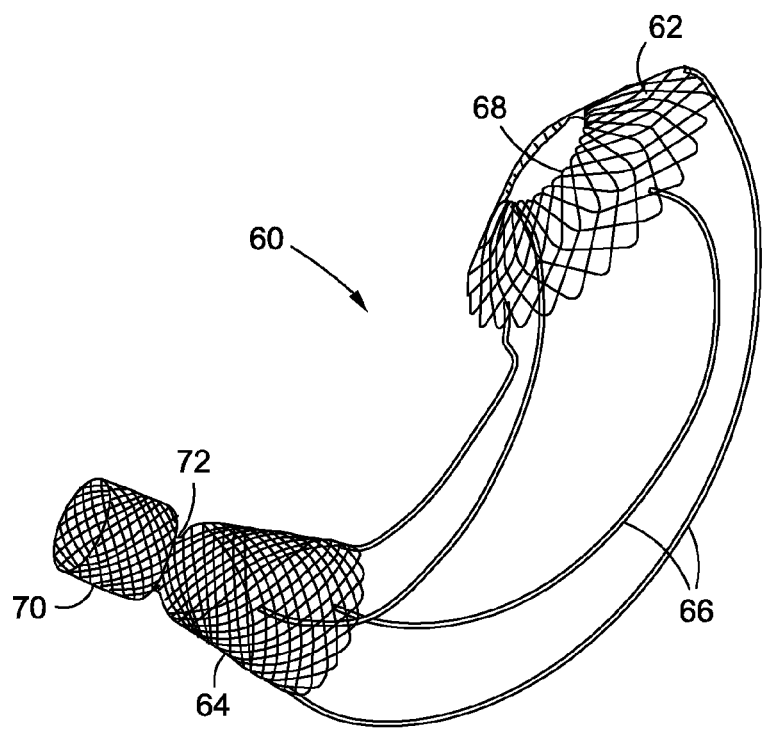
FIG. 4 is a perspective view of the implant of FIG. 3.

Figure 3 illustrating a different stomach-spanning intragastric obesity implant 60 having a cardia flange 62 and a generally tubular antrum stent 64 connected by struts 66, while FIG. 4 shows the implant by itself. The cardia flange 62 is a flexible, flat partial conical ring that includes a central through hole 68 centered at the esophageal sphincter through which food passes. In the illustrated embodiment the cardia flange 62 comprises a braided wire mesh, such as from NITINOL covered with a soft silicone. Likewise, the antrum stent 64 comprises a braided wire mesh, such as from NITINOL covered with a soft silicone. It should be noted that other configurations for the cardia flange 62 and the antrum stent 64 are contemplated; for instance, they may alternatively be a solid silicone member with wire reinforcements.

In the illustrated embodiment, the implant 60 further comprises a duodenal stent 70 connected in series with the antrum stent 64 at a narrow neck region 72. The combined somewhat hourglass shape of the antrum stent 64, neck region 72, and duodenal stent 70 is adapted to conform closely to the antrum, pylorus and upper end of the duodenum. The duodenal stent 70 is considered optional.

The struts 66 connecting the cardia flange 62 and antrum stent 64 are preferably flexible enough to straighten out and be passed transorally down an access tube, while also being somewhat stiff to provide light pressure to both the cardia flange 62 and antrum stent 64 on each end. In this way, the cardia flange 62 contacts and stimulates the cardia, and antrum stent 64 contacts and stimulates the antrum, both helping to induce a feeling of satiety. In a preferred embodiment there is no esophageal stent, and the entire device resides below the esophageal sphincter. As stated above, the duodenal stent 70 is optional and in a configuration without it the implant 60 remains anchored in place just by virtue of the stiffness of the struts 66 applying pressure to both the cardia flange 62 and antrum stent 64.

In one embodiment, the central through hole 68 of the cardia flange 62 is large enough to avoid impeding flow of food and liquid into the stomach. Likewise, the antrum stent 64 and duodenal stent 70 may be sized to permit free flow of chime, or may be slightly undersized so as to delay gastric emptying, and thus slow the eating process. All of the tubular elements and the length of the struts 66 may be custom sized to fit a variety of patients.

As with the other embodiments, the implant 60 is implanted transorally, across the gastro-esophageal (G-E) junction, during a minimally invasive gastroendoscopic surgical procedure. The implant 60 may easily be compressed within a delivery tube and advanced through the esophagus to be deployed within the stomach. The NITINOL stents easily compress down to pass through the access tube, with the struts 66 therebetween. One sequence includes first expelling the antrum stent 64, and duodenal stent 70 if included, at the antrum, and gradually withdrawing the access tube to release the struts 66 and then the cardia flange 62. Withdrawal through a similar tube using a grabber is also contemplated.

It should also be stated that any of the embodiments described herein may utilize materials that improve the efficacy of the implant. For example, a number of elastomeric materials may be used including, but not limited to, rubbers, fluorosilicones, fluoroelastomers, thermoplastic elastomers, or any combinations thereof. The materials are desirably selected so as to increase the durability of the implant and facilitate implantation of at least six months, and preferably more than 1 year.

Material selection may also improve the safety of the implant. Some of the materials suggested herein, for example, may allow for a thinner wall thickness and have a lower coefficient of friction than the implant.

The implantable devices described herein will be subjected to clinical testing in humans. The devices are intended to treat obesity, which is variously defined by different medical authorities. In general, the terms "overweight" and "obese" are labels for ranges of weight that are greater than what is generally considered healthy for a given height. The terms also identify ranges of weight that have been shown to increase the likelihood of certain diseases and other health problems. Applicants propose implanting the devices as described herein into a clinical survey group of obese patients in order to monitor weight loss.

The clinical studies will utilize the devices described above in conjunction with the following parameters.

Materials:
a. Silicone materials used include 3206 silicone for any shells, inflatable structures, or otherwise flexible hollow structures. Any fill valves will be made from 4850 silicone with 6% $BaSo_4$. Tubular structures or other flexible conduits will be made from silicone rubber as defined by the Food and Drug Administration (FDA) in the Code of Federal Regulations (CFR) Title 21 Section 177.2600.

Purposes:
i. the devices are for human implant,
ii. the devices are intended to occupy gastric space while also applying intermittent pressure to various and continually changing areas of the stomach;
iii. the devices are intended to stimulate feelings of satiety, thereby functioning as a treatment for obesity.

General Implant Procedures:
i. The device is intended to be implanted transorally via endoscope into the corpus of the stomach.
ii. Implantation of the medical devices will occur via endoscopy.
iii. Nasal/Respiratory administration of oxygen and isoflurane to be used during surgical procedures to maintain anesthesia as necessary.

One exemplary implant procedure is listed below.
i. Perform preliminary endoscopy on the patient to examine the GI tract and determine if there are any anatomical anomalies which may affect the procedure and/or outcome of the study.
ii. Insert and introducer into the over-tube.
iii. Insert a gastroscope through the introducer inlet until the flexible portion of the gastroscope is fully exited the distal end of the introducer.
iv. Leading under endoscopic vision, gently navigate the gastroscope, followed by the introducer/over-tube, into the stomach.
v. Remove gastroscope and introducer while keeping the over-tube in place.
vi. OPTIONAL: Place the insufflation cap on the over-tubes inlet, insert the gastroscope, and navigate back to the stomach cavity.
vii. OPTIONAL: Insufflate the stomach with air/inert gas to provide greater endoscopic visual working volume.
viii. Collapse the gastric implant and insert the lubricated implant into the over-tube, with inflation catheter following if required.
ix. Under endoscopic vision, push the gastric implant down the over-tube with gastroscope until visual confirmation of deployment of the device into the stomach can be determined.

x. Remove the guide-wire from the inflation catheter is used.

xi. If inflated: Inflate the implant using a standard Bio-Enterics Intragastric Balloon System ("BIB System") Fill kit.

xii. Using 50-60 cc increments, inflate the volume to the desired fill volume.

xiii. Remove the inflation catheter via over-tube.

xiv. Inspect the gastric implant under endoscopic vision for valve leakage, and any other potential anomalies. Record all observations.

xv. Remove the gastroscope from over-tube.

xvi. Remove the over-tube from the patient.

End Point Criteria:

Weight Loss

Comprehensive Metabolic Panel (CMP)

HbAlC

Lipid Panel

Tissue Samples/Response

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references may have been made to patents and printed publications in this specification. Each of the above-cited references and printed publications are individually incorporated herein by reference in their entirety.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A passive intragastric obesity treatment implant, comprising:
   a tube having:
      a tubular body of a length sufficient to extend longitudinally between an esophageal sphincter at a proximal end of the tubular body and a pyloric sphincter at a distal end of the tubular body upon implantation in the stomach, the tubular body having perforations therein to permit ingress of stomach juices;
      a first set of longitudinal slits formed in a wall of the tube adjacent the proximal end of the tubular body and forming a first collapsible member;
      a second set of longitudinal slits formed in the wall of the tube adjacent the distal end of the tubular body and forming a second collapsible member;
      an esophageal stent sized to anchor within the esophagus just above the esophageal sphincter, the esophageal stent extending proximally from the first set of longitudinal slits, the first set of longitudinal slits disposed between the esophageal stent and the tubular body;
      a distal sleeve forming a duodenal tube, the distal sleeve extending distally from the second set of longitudinal slits, the second set of longitudinal slits disposed between the distal sleeve and the tubular body; and a bulbous flange surrounding and connected to the distal end of the tubular body, the bulbous flange having a size that prevents passage through the pyloric sphincter, the implant being formed of materials that permit it to be compressed into a substantially linear transoral delivery configuration and that will resist degradation over a period of at least six months within the stomach.

2. The implant of claim 1, further including:

an enlargement surrounding the duodenal tube and sized to prevent passage through the pyloric sphincter.

3. The implant of claim 2, wherein the duodenal tube and enlargement extend only up to 5-10 cm in length.

4. The implant of claim 1, further including a set of perforations along the tubular body between the first set of longitudinal slits and the second set of longitudinal slits the to allow ingress of digestive stomach juices.

5. The implant of claim 1, wherein the bulbous flange is molded with relatively thick walls to maintain its as-molded shape without inflation.

6. The implant of claim 1, wherein the entire implant is made of silicone.

* * * * *